United States Patent
Yoshikawa et al.

(10) Patent No.: US 9,359,274 B2
(45) Date of Patent: Jun. 7, 2016

(54) METHOD FOR PRODUCING 1,3,3,3-TETRAFLUOROPROPENE

(71) Applicant: Central Glass Company, Limited, Ube-shi, Yamaguchi (JP)

(72) Inventors: Satoshi Yoshikawa, Saitama (JP); Fuyuhiko Sakyu, Kawagoe-shi (JP); Naoto Takada, Saitama (JP)

(73) Assignee: Centeral Glass Company, Limited, Ube-shi (JP)

( * ) Notice: Subject to any disclaimer, the term of this patent is extended or adjusted under 35 U.S.C. 154(b) by 0 days.

(21) Appl. No.: 14/411,277

(22) PCT Filed: Jun. 27, 2013

(86) PCT No.: PCT/JP2013/067626
§ 371 (c)(1),
(2) Date: Dec. 24, 2014

(87) PCT Pub. No.: WO2014/003109
PCT Pub. Date: Jan. 3, 2014

(65) Prior Publication Data
US 2015/0321978 A1 Nov. 12, 2015

(30) Foreign Application Priority Data

Jun. 28, 2012 (JP) ................. 2012-144913
Jun. 12, 2013 (JP) ................. 2013-124002

(51) Int. Cl.
*C07C 17/25* (2006.01)
*C07C 17/23* (2006.01)
*C07C 17/383* (2006.01)
*B01J 21/06* (2006.01)
*B01J 21/04* (2006.01)
*B01J 23/26* (2006.01)
*B01J 23/86* (2006.01)
*C07C 17/38* (2006.01)

(52) U.S. Cl.
CPC ............. *C07C 17/25* (2013.01); *B01J 21/04* (2013.01); *B01J 21/066* (2013.01); *B01J 23/26* (2013.01); *B01J 23/868* (2013.01); *C07C 17/38* (2013.01); *C07C 17/383* (2013.01); *C07C 17/23* (2013.01)

(58) Field of Classification Search
CPC ................................ C07C 17/25; C07C 17/23
USPC .................................................. 570/156, 157
See application file for complete search history.

(56) References Cited

U.S. PATENT DOCUMENTS

| | | | |
|---|---|---|---|
| 2,480,560 A | 8/1949 | Benning et al. | |
| 6,369,284 B1 | 4/2002 | Nappa et al. | |
| 2009/0099395 A1 | 4/2009 | Sakyu et al. | |
| 2009/0270661 A1 | 10/2009 | Wang et al. | |

FOREIGN PATENT DOCUMENTS

| | | |
|---|---|---|
| JP | 9-67281 A | 3/1997 |
| JP | 11-14002 A | 1/1999 |
| JP | 11-140002 A | 5/1999 |
| JP | 2001-509503 A | 7/2001 |
| JP | 2001-509803 A | 7/2001 |
| JP | 2008-19243 A | 1/2008 |
| JP | 2009-263365 A | 11/2009 |

OTHER PUBLICATIONS

R.N. Haszeldine et al., J. Chem. Soc. 1953, pp. 1199-1206; CA 485787f.
I.L. Knunyants et al., Izvest. Akad. Nauk S.S.S.R., Otdel. Khim. Nauk. 1960, pp. 1412-1418; CA 55, 349f.
International Search Report (PCT/ISA/210) dated Aug. 13, 2013 with English-language translation (Four (4) pages).

*Primary Examiner* — Elvis O Price
(74) *Attorney, Agent, or Firm* — Crowell & Moring LLP

(57) ABSTRACT

Provided is a method for causing a dehydrofluorination reaction of 1,1,1,3,3-pentafluoropropane in the gas phase and in the presence of a catalyst thereby producing 1,3,3,3-tetrafluoropropene. In this method, the reaction is carried out at a pressure inside the reaction system of from 0.001 to 90 kPa (absolute pressure) at a reaction temperature ranging from 250 to 600° C.

5 Claims, No Drawings

METHOD FOR PRODUCING 1,3,3,3-TETRAFLUOROPROPENE

TECHNICAL FIELD

The present invention relates to a method for producing 1,3,3,3-tetrafluoropropene.

BACKGROUND OF THE INVENTION

As a method for producing 1,3,3,3-tetrafluoropropene, there have conventionally been known various methods such as a process for dehydroiodinating 1,3,3,3-tetrafluoro-1-iodopropane with an alcoholic potassium hydroxide (Non-Patent Publication 1), a process for dehydrofluorinating 1,1,1,3,3-pentafluoropropane (HFC-245fa) in dibutyl ether with potassium hydroxide (Non-Patent Publication 2) and the like. Though the process of dehydrohalogenation with potassium hydroxide as proposed by Non-Patent Publications 1 and 2 is superior in reactivity and selectivity, it is necessary to use a solvent and potassium hydroxide of a stoichiometric amount or more. Moreover, it was confirmed from the result of the reaction that an enormously large amount of potassium salt was produced. Thus the above-mentioned process has various difficulties in industrial application.

On the other hand, studies on a dehydrofluorination reaction in the gas phase and the like have been made also. As an example of a dehydrofluorination reaction using a typical fluoroalkane compound in the gas phase, Patent Publication 1 discloses a process for producing a corresponding propene by bringing 1,1,1,3,3,3-hexafluoropropane into a gaseous condition and making it contact with activated carbon or a chromium oxide catalyst, and Patent Publication 2 discloses a process for bringing fluoroethane into contact with activated carbon and initiating a thermal decomposition thereon.

Additionally, Patent Publication 3 discloses a process of dehydrofluorinating 1,1,1,3,3-pentafluoropropane in the gas phase in the presence of a catalyst in the use of a zirconium compound-carried catalyst where a zirconium compound is carried on a metal oxide or activated carbon thereby obtaining 1,3,3,3-tetrafluoropropene.

REFERENCES ABOUT PRIOR ART

Patent Documents

Patent Publication 1: Japanese Patent Application Publication No. 9-67281
Patent Publication 2: U.S. Pat. No. 2,480,560
Patent Publication 3: Japanese Patent Application Publication No. 2008-019243

Non-Patent Documents

Non-Patent Publication 1: R. N. Haszeldine et al., J. Chem. Soc. 1953, 1199-1206; CA 48 5787f
Non-Patent Publication 2: I. L. Knunyants et al., Izvest. Akad. Nauk S.S.S.R., Otdel. Khim. Nauk. 1960, 1412-18; CA 55, 349f

SUMMARY OF THE INVENTION

Problems to be Solved by the Invention

A dehydrofluorination reaction of a fluoroalkane compound in the gas phase requires strict reaction conditions, but nevertheless the conversion ratio is not always so high. For example, in the process disclosed by Patent Publication 1 where 1,1,1,3,3,3-hexafluoropropane is brought into a gaseous condition in the presence of activated carbon or a chromium oxide catalyst, the conversion ratio was obtained at about 4 to 50% while the selectivity was quantitatively obtained.

Though Patent Publication 2 discloses the process for causing a thermal decomposition at considerably high temperatures (about 750 to 900° C.), the conversion ratio in this process is also up to the extent of 40%.

The process discussed in Patent Publication 3 may be a useful process at a glance since a high conversion ratio is sometimes obtained depending on the kind of the used metal, but in most cases the conversion ratio is low (about 10 to 60%). In the reaction disclosed by this document, 1,1,1,3,3-pentafluoropropane as the starting material is to remain in the reaction system. It is assumed not easy to separate the remaining material from the target compound 1,3,3,3-tetrafluoropropene (because of both are close to each other in boiling point). If considering performing purification, it is necessary to further reduce the content of 1,1,1,3,3-pentafluoropropane in the target compound.

In addition, the conventional processes employ a significantly endothermic reaction where the temperature is suddenly decreased at the inlet of a catalyst bed, in which the catalyst becomes overloaded at around the inlet. Therefore an efficient reaction style which is moderate in view of temperature distribution is desired.

In order to improve the conversion ratio in the above-mentioned dehydrofluorination reaction, the reaction condition is needed to be modified more strictly. Furthermore, the reaction requires so high temperatures that it is expected to be considerably difficult to execute an industrial production, in view of conversion of the product to tar, carbonization of the product, and the durability of the reactor.

An object of the present invention is to provide a method for producing the target compound 1,3,3,3-tetrafluoropropene at high conversion ratio on an industrial scale with efficiency.

Means for Solving the Problems

As a result of having made studies eagerly, the present inventors have achieved a finding that, in a method for causing a dehydrofluorination reaction of 1,1,1,3,3-pentafluoropropane in the presence of a catalyst thereby to produce 1,3,3,3-tetrafluoropropene, when the reaction is carried out at a pressure inside the reaction system of from 0.001 to 90 kPa (absolute pressure) (in this specification, the same shall apply hereinafter) at a reaction temperature ranging from 250 to 600° C., this reaction proceeds with high conversion ratio and selectivity in the presence of any kind of metal catalyst.

The present inventors have also found that the reaction can efficiently proceed under the thus specified reaction conditions even if the contact time of reaction according to the present invention is short, thereby achieving the completion of the present invention.

In the case of conducting the gas phase reaction under a reduced pressure, it is expected not only that the contact time becomes short but also that the heat conduction becomes deteriorated as compared with a reaction made at normal pressure. In spite of this, the present inventors carried out the reaction under the specified conditions thereby achieving a finding that the reaction proceeds efficiently as compared with a reaction under normal pressure even if the contact time is short. Additionally, the reaction can proceed at high conversion ratio, so that the load of separating 1,1,1,3,3-pentafluoropropane from 1,3,3,3-tetrafluoropropene close to 1,1,1,3,3-pentafluoropropane in boiling point becomes significantly lessened.

Furthermore, the contact time is extensively shortened by reducing pressure, which therefore allows an industrial-scale production in a short time. Thus the method according to the present invention also possesses an industrial superiority.

More specifically, the present invention provides the following inventions as discussed in [Invention 1] to [Invention 8].

[Invention 1]

A method for producing 1,3,3,3-tetrafluoropropene, characterized by comprising the steps of causing a dehydrofluorination reaction of 1,1,1,3,3-pentafluoropropane in the gas phase and in the presence of a catalyst thereby producing 1,3,3,3-tetrafluoropropene, wherein the reaction is carried out at a pressure inside the reaction system of from 0.001 to 90 kPa (absolute pressure) at a reaction temperature ranging from 250 to 600° C.

[Invention 2]

A production method as discussed in Invention 1, wherein the catalyst is a metal compound-carried catalyst where a metal compound is carried on a metal oxide or activated carbon, or a metal oxide.

[Invention 3]

A production method as discussed in Invention 2, wherein the metal compound comprises at least one kind selected from the group consisting of aluminum, titanium, chromium, manganese, nickel, copper, cobalt, zirconium, niobium, molybdenum, tin, antimony and tantalum.

[Invention 4]

A production method as discussed in Invention 2 or 3, wherein the metal oxide is at least one kind selected from the group consisting of alumina, zirconia, titania and magnesia.

[Invention 5]

A production method as discussed in any of Inventions 2 to 4, characterized in that the metal compound is a metal halide or a metal oxyhalide.

[Invention 6]

A production method as discussed in any of Inventions 2 to 5, characterized in that the metal oxide is obtained by a modification treatment with hydrogen fluoride, hydrogen chloride or a chlorinated and fluorinated hydrocarbon.

[Invention 7]

A production method as discussed in any of Inventions 1 to 6, further comprising the steps of separating and removing hydrogen fluoride from a reaction mixture produced by the dehydrofluorination reaction of 1,1,1,3,3-pentafluoropropane, the reaction mixture containing 1,3,3,3-tetrafluoropropene, organic impurities and hydrogen fluoride; and subjecting the mixture obtained after removing hydrogen fluoride to distillation.

[Invention 8]

A production method as discussed in Invention 7, characterized in that the separation of hydrogen fluoride is carried out by bringing hydrogen fluoride into contact with sulfuric acid.

Effects of the Invention

The method for producing 1,3,3,3-tetrafluoropropene according to the present invention uses an industrially available 1,1,1,3,3-pentafluoropropane as the raw material and causes a reaction under preferable reaction conditions, thereby bringing about the effect of producing 1,3,3,3-tetrafluoropropene at high conversion ratio.

Mode(s) for Carrying Out the Invention

The method for producing 1,3,3,3-tetrafluoropropene according to the present invention will hereinafter be discussed in detail. Incidentally, the scope of the present invention is not limited to the following explanations, and modifications and variations of the following examples will occur within a range not affecting the light of the present invention. In addition, any publication cited in the specification of the present application e.g. prior art documents, unexamined patent publications, examined patent publications and other patent documents is involved in the specification as references.

By the way, 1,3,3,3-tetrafluoropropene has stereoisomers by itself and takes on a cis isomer (Z isomer), a trans isomer (E isomer) and a cis/trans mixture (E/Z isomers). The cis isomer may be referred to as 1234Z and the trans isomer may be referred to as 1234E. In the case of using E/Z mixture or in the case of not distinguishing the E/Z isomerism, 1,3,3,3-tetrafluoropropene may be referred to as 1234.

A catalyst used in the present invention is a metal compound-carried catalyst where a metal compound is carried on a metal oxide or activated carbon, or a metal oxide The catalyst is such that a high-valence metal that belongs to any of Groups 4 to 15 of the periodic table is carried as a metal on a carrier, and more specifically, it comprises at least one kind selected from the group consisting of aluminum, titanium, chromium, manganese, nickel, copper, cobalt, zirconium, niobium, molybdenum, tin, antimony and tantalum.

The metal compound used for preparing the metal compound-carried catalyst is at least one kind of a metal halide or a metal oxyhalide selected from the group consisting of fluorides, chlorides, fluorinated chlorides, oxyfluorides, oxychlorides or oxyfluorinated chlorides of a metal compound.

A metal oxide useful as a carrier is at least one kind selected from the group consisting of alumina, zirconia, titania and magnesia. Moreover, activated carbon useful as another carrier may be selected from various kinds of them which are commercially available. As an example, it is possible to cite activated carbon produced from bituminous coal (for example, granulated activated carbon Calgon CAL (available from Toyo Calgon Corporation), palm husk charcoal (for example, available from Japan EnviroChemicals, Ltd.) or the like; however, it will be understood that activated carbon is not limited to these kinds and these makers.

A process of preparing the metal compound-carried catalyst according to the present invention is not limited. It may be prepared by previously subjecting a carrier (a metal oxide, activated carbon or both) to a modification treatment with halogen, for example by hydrogen fluoride, hydrogen chloride or a chlorinated and fluorinated hydrocarbon at a temperature not lower than a prescribed reaction temperature, and then impregnating the modified compound with a solution in which a soluble metal compound which is in the form of nitrate, chloride, oxyhalide or the like is dissolved or spraying the same.

As a concrete example of the modification treatment with halogen, fluorination process will be discussed. Fluorination process can be performed by any manner; however, for example, fluorinated alumina can be prepared by flowing hydrogen fluoride through alumina (which is commercially available for drying use or catalyst carrier use) in the gas phase while heating it, or by spraying a hydrogen fluoride aqueous solution on alumina at around room temperature or impregnating alumina with the above solution and then drying it.

Other carrying processes are not particularly limited and required only to be one in which a metal halide adheres to activated carbon. In a case of a compound that serves as liquid at around room temperature, such as antimony pentachloride, tin tetrachloride, titanium tetrachloride and the like, it is possible to adhere the liquid compound directly to activated carbon on which an after-mentioned pretreatment (such as a treatment with a basic substance, acid or hot water and dehydration treatment) has been made as necessary, by a process exemplified by dropping as it is, spraying, immersion and the like.

Subsequently, the thus obtained catalyst carrier to which the metal compound adheres is dried by heat and/or pressure reduction. Then, the catalyst carrier to which the metal halide adheres is brought into contact with hydrogen fluoride, chlorine, hydrogen chloride, chlorinated and fluorinated hydrocarbon or the like under heat, thereby preparing the catalyst.

In addition to the metal compound-carried catalyst, the present invention can also accept the single use of a metal oxide as the catalyst. The metal oxide is at least one kind selected from the group consisting of alumina, zirconia, titania and magnesia. It will be understood that the metal oxide may be used as it is or upon having been subjected to a modification treatment with halogen by hydrogen fluoride, hydrogen chloride, a chlorinated and fluorinated hydrocarbon or the like in advance of the dehydrofluorination reaction, as in the case of the metal compound-carried catalyst.

The catalyst to be used in the present invention may employ alumina, fluorinated alumina, aluminum fluoride, activated carbon and the like as the carrier. Of these carriers, particularly preferable examples are a zirconium compound-carried fluorinated alumina, fluorinated alumina, a chromium compound-carried catalyst and zirconia.

The amount of the metal compound being carried on the carrier ("the carried amount"), which corresponds to the ratio relative to the total amount of the metal compound and the carrier, is normally 0.1 to 80 wt %, preferably 1 to 40 wt %. A metal compound to be carried on a carrier and behaves as a soluble substance is exemplified by nitrates, phosphates, chlorides, oxides, oxychlorides, oxyfluorides, oxyhalides and the like of the metal which are soluble in a solvent such as water, hydrochloric acid, aqueous ammonia, ethanol and acetone. Incidentally, the catalyst according the present invention may be one previously dried by being heated to 300 to 400° C., which is one of the preferable embodiments of the present invention.

The present invention is characterized by bringing the reaction under a pressure-reduced condition and within the after-mentioned temperature range. The pressure is normally 0.001 to 90 kPa, preferably 0.001 to 50 kPa, more preferably 0.001 to 20 kPa.

When having conducted the reaction under a vacuum condition at absolute pressure of about 1 kPa, there was exhibited an extremely great conversion ratio even though the contact time is 0.1 second (details will be discussed below). This means that the productivity was equal or superior to that in a reaction made at normal pressure, which can be cited as one of the particularly remarkable effects of the present invention.

A pressure-reducing device to be used at the time of bringing the reaction system under a pressure-reduced condition is not particularly limited so long as it can reduce the pressure of the interior of a reactor to a desired pressure. As an example of the pressure-reducing device, it is possible to cite a power pump, an ejector (i.e. an aspirator that harnesses the Venturi effect) and so on.

Furthermore, it is preferable to perform cooling in the reaction system in advance of the pressure reduction. Cooling in the use of a heat exchanger to a temperature of around −10 to 10° C. is preferably performed, though cooling by itself is also acceptable.

It is an important characteristic that the present invention is carried out within the above-mentioned pressure range at a specified reaction temperature. The reaction temperature is normally 250 to 600° C., preferably 300 to 500° C., more preferably 300 to 400° C. When the reaction temperature is lower than 250° C., the reaction is to slow down even at the specified reaction pressure so as not to be practical. If the reaction temperature exceeds 600° C. the reaction proceeds rapidly, but the catalyst life is to be shortened and a decomposition product may be produced so as to reduce the selectivity of 1,3,3,3-tetrafluoropropene. The reaction according to the present invention can sufficiently be developed under a specified condition (or under a pressure-reduced condition), so that temperatures exceeding 600° C. is not particularly required.

In the present invention where the reaction is carried out upon bringing the interior of the reactor under a pressure-reduced condition, it is preferable to adequately heat the interior of the reactor to the above-mentioned reaction temperature range in advance of the reaction.

In the method according to the present invention, 1,1,1,3,3-pentafluoropropane to be fed into a reaction region may be supplied together with an inert gas such as nitrogen, argon and helium.

The present invention is conducted under a pressure-reduced condition as distinct from conventional techniques, and therefore the reaction according to the present invention can sufficiently proceed even if the contact time is extensively short. More specifically, under the above-mentioned pressure-reduced condition, the contact time is usually between 0.01 to 5 seconds, particularly preferably between 0.01 to 1 second.

An equation for calculating the contact time is as follows.

[Equation for calculating contact time]

$$\text{Contact time (sec)} = \text{Amount of catalyst (ml)} / \{\text{Supplied raw material (by mass in a state of gas) (ml/sec)}\}$$

If the mas of gas (described as "mass in a state of gas") is a value of standard condition, "a contact time in terms of standard condition" is obtained. It the mas of gas is a value of real condition, "a contact time in terms of real condition" is obtained.

When the amount of the catalyst is 1000 ml and the temperature is 300° C. and the amount of the supplied raw material is 17.9 g/min, there is obtained a contact time in terms of standard condition of about 20 seconds. However, a contact time will be discussed in terms of real condition, in consideration of a temperature condition and a pressure condition. A contact time at a temperature of 300° C. and the following pressure will be shown below.

Normal pressure (101 kPa): about 10 seconds
Reduced pressure (50 kPa): about 5 seconds
Reduced pressure (10 kPa): about 1 second
Reduced pressure (1 kPa): about 0.1 second In the case of performing a comparison between a conventional method (normal pressure method) and the method according to the present invention by means of the same reaction device and the same supply rate of 1,1,1,3,3-pentafluoropropane, there is obtained in the present invention a shorter contact time. The reaction made under a pressure-reduced condition according to the present invention increases the volume of the gas per unit and therefore it apparently requires a scale-up of facilities; in fact, however, the pressure reduction method where the contact time is short can increase the throughput of the raw material per unit time. By conducting the reaction under a pressure-reduced condition according to the present invention, it becomes possible to improve the reaction rate only without the throughput being changed.

The reactor used in the present invention is required only to be one formed of a material having a heat resistance and a rust resistance against hydrogen fluoride, hydrogen chloride and the like and usable under a pressure-reduced condition. For example, the reactor is preferably formed of stainless steel, Hastelloy, Monel, platinum or the like. Additionally, the reactor may be formed of a material that has been subjected to lining with these metals.

A product having been put through the reaction of this step and discharged from the reactor (i.e., a product containing 1,3,3,3-tetrafluoropropene) is obtained in the form of a reaction mixture which contains cis-1,3,3,3-tetrafluoropropene, trans-1,3,3,3-tetrafluoropropene and other organic impurities. In the reaction mixture, an acid gas such as hydrogen fluoride is also contained.

Since the obtained reaction mixture thus contains hydrogen fluoride, it is necessary to remove hydrogen fluoride therefrom. As an operation for removing hydrogen fluoride (a process for removing hydrogen fluoride), it is possible in the present invention to bring the product into contact with a matter capable of absorbing hydrogen fluoride e.g. sulfuric acid and tertiary amine, or to rinse the product with water, an alkaline aqueous solution or the like thereby removing hydrogen fluoride. In the case of using water, hydrogen fluoride can sufficiently be removed also by blowing the above-mentioned reaction mixture into water.

Additionally, hydrogen fluoride can be separated by forming a complex between hydrogen fluoride and potassium fluoride, sodium fluoride or the like. The complex is reacted with a calcium salt such as calcium chloride, calcium hydroxide, calcium oxide, calcium carbonate and the like or with an aqueous solution of these, thereby conducting a treatment for fixing calcium fluoride ($CaF_2$) to allow removal of hydrogen fluoride from the mixture.

The amount of sulfuric acid can suitably be adjusted by the skilled artisan since it depends on the amount of hydrogen fluoride contained in the reaction mixture. The minimum necessary amount of sulfuric acid may be determined from the solubility of hydrogen fluoride in 100% sulfuric acid by using a graph of the solubility relative to temperature (at 30° C., for example, about 34 g of hydrogen fluoride is dissolved in 100 g of 100% sulfuric acid).

The purity of sulfuric acid is not particularly limited. However, sulfuric acid preferably has a purity of not lower than 50%, more preferably from about 98% to 100%. Usually, a commercially available sulfuric acid for industrial use (98%) may be used.

When separating hydrogen fluoride, it is possible to employ any form of device and any operation method as long as absorption of hydrogen fluoride into sulfuric acid is feasible. A method of charging a bath with sulfuric acid and then blowing the reaction mixture in a gas state thereinto, a method of blowing the reaction mixture into a sulfuric acid scrubber filled with a filler so as to bring the gas and sulfuric acid into countercurrent contact, and the like are employable. However, a separation method is not limited to the above as far as absorption of hydrogen fluoride into sulfuric acid is feasible, and therefore it is also possible to adopt other method.

In a case of treating the product with sulfuric acid, for instance, the removed hydrogen fluoride may be separated, recovered and reused. More specifically, it is also possible to use this hydrogen fluoride as a starting material for the other reaction while reusing sulfuric acid in a step of extracting hydrogen fluoride.

In a case of using tributylamine ($Bu_3N$), a salt formed between tributylamine and hydrogen fluoride ($Bu_3N.HF$) may be rinsed with a basic aqueous solution and reused in absorption of hydrogen fluoride.

For example, hydrogen fluoride may be used as a reaction reagent at the time of converting trans-1,3,3,3-tetrafluoropropene produced together with cis-1,3,3,3-tetrafluoropropene into 1,1,1,3,3-pentafluoropropane.

Then, the reaction mixture from which hydrogen fluoride has been separated is subjected to distillation. With this, it becomes possible to separate cis and trans isomers of 1,3,3,3-tetrafluoropropene from each other. Distillation may be conducted either in a continuous style or in a batch style. Concerning a pressure during the operation, either normal pressure (atmospheric pressure) or applied pressure is acceptable but it is preferable to select a pressure condition capable of increasing the condensation temperature in distillation. A distillation column is required only to have a wall which is inert against a distillate. The wall may be formed of glass or stainless steel. Furthermore, a distillation column formed of a substrate (e.g. steel) that has been subjected at inside to lining with tetrafluoroethylene resin, chlorotrifluoroethylene resin, vinylidene fluoride resin, PFA resin or glass is also acceptable. The distillation column may be of the multi-tray type or may be one packed with a filler such as Raschig rings, Lessing rings, Dixon rings, Pall rings, Intalox saddles and Sulzer packing.

Cis and trans isomers of 1,3,3,3-tetrafluoropropene can be separated from each other as mentioned above. However, there are some cases where 1,1,1,3,3-pentafluoropropane is contained in cis-1,3,3,3-tetrafluoropropene as will be discussed in the following Examples. This is derived from the fact that cis-1,3,3,3-tetrafluoropropene and 1,1,1,3,3-pentafluoropropane exhibit an azeotropic composition as well known by conventional techniques. By employing the undermentioned method, it becomes possible to obtain not only cis-1,3,3,3-tetrafluoropropene but also the trans isomer with high purity as compared to conventional techniques.

For example, cis-1,3,3,3-tetrafluoropropene in which 1,1,1,3,3-pentafluoropropane is contained is reacted with a base, followed by performing distillation. As a result of this, it becomes possible to obtain cis-1,3,3,3-tetrafluoropropene which does not substantially contain 1,1,1,3,3-pentafluoropropane.

Incidentally, "cis-1,3,3,3-tetrafluoropropene which does not substantially contain 1,1,1,3,3-pentafluoropropane" means cis-1,3,3,3-tetrafluoropropene where a mole ratio represented by 1,1,1,3,3-pentafluoropropane/cis-1,3,3,3-tetrafluoropropene is smaller after the reaction with base than that before the reaction with base. The mole ratio is normally not larger than 1/100, preferably not larger than 1/500, more preferably not larger than 1/1000.

The base to be used is hydroxide of an alkali metal, or hydroxide of an alkaline earth metal. An alkali metal discussed herein refers to lithium, sodium, potassium, rubidium or cesium, and an alkaline earth metal refers to magnesium, calcium or strontium.

Concerning hydroxide of an alkali metal and hydroxide of an alkaline earth metal, it is possible to cite concrete compounds such as lithium hydroxide, sodium hydroxide, potassium hydroxide, calcium hydroxide, magnesium hydroxide and strontium hydroxide. Of these, preferable compounds are potassium hydroxide, sodium hydroxide and calcium hydroxide. In particular, potassium hydroxide and sodium hydroxide are more preferably employed because these are reasonable and industrially available on a large scale.

Moreover, the base to be used may be used singly or in combination of two or more kinds.

The base to be used is required to have an amount of at least 1 mol in terms of 1 mol, relative to the reaction mixture containing cis-1,3,3,3-tetrafluoropropene and 1,1,1,3,3-pentafluoropropane. In usual cases the amount of the base may suitably be selected within a range from 1 to 10 mol. However, it is preferably 1 to 4 mol, more preferably 1 to 2 mol. A base larger than 10 mol is also acceptable but there is no remarkable merit in using such a large amount.

In some cases of using a base smaller than 1 mol relative to 1 mol of the compound represented by the formula [1], the conversion ratio in the reaction may be reduced.

The base specified as above is in the form of a solid at room temperature and normal pressure, and therefore it may be added to at least one kind of solvent thereby being provided to the reaction in the form of a solution as necessary, which is suitably selected by the skilled artisan. The solvent to be used is not particularly limited unless it committed to the reaction, and exemplified by: alkanes such as n-pentane, n-hexane, n-heptane and n-octane; aromatic hydrocarbons such as benzene, toluene and xylene; ethers such as diethyl ether, tetrahydrofuran and dioxane; halogenated hydrocarbons such as dichloromethane and chloroform; ketones such as acetone, methyl ethyl ketone and methyl isobutyl ketone; nitriles such as acetonitrile, propionitrile and butyronitrile; amides such as N,N-dimethylformamide (DMF), N,N-dimethylacetamide (DMAC) and hexamethylphosphoric triamide (HMPA); glycols such as ethylene glycol, diethylene glycol, ethylene glycol monomethyl ether and ethylene glycol monoacetate; alcohols such as methanol, ethanol and 2-propanol; water; and the like. These solvents may be used singly or in combination of two or more kinds.

Though discussed below, an example where potassium hydroxide is used as the base and water is used as the solvent is one of particularly preferable embodiments of the present invention.

In addition to the solvent, it is also possible to use a phase transfer catalyst as an additive. The phase transfer catalyst is preferably used since the reaction is accelerated particularly if hydroxide of an alkali metal is used as the base.

As the phase transfer catalyst, it is possible to employ crown ether, cryptand or an onium salt. Crown ether envelops a metal cation thereby improving reactivity. For example, there are combinations of potassium cation and 18-crown-6, sodium cation and 15-crown-5, lithium cation and 12-crown-4, and so on. Additionally, a dibenzo derivative of crown ether, a dicyclohexano derivative of the same etc. are also useful.

Cryptand is a polycyclic and macrocyclic chelating agent and forms a complex (a cryptate) with potassium cation, sodium cation, rubidium cation, cesium cation, lithium cation or the like thereby being able to activate the reaction. It is possible to cite 4,7,13,18-tetraoxa-1,10-diazabicyclo[8.5.5] icosane ("Cryptand 211"), 4,7,13,16,21,24-hexaoxa-1,10-diazabicyclo[8.8.8]hexacosane ("Cryptand 222") and the like.

The onium salt is exemplified by quaternary ammonium salts and quaternary phosphonium salts. For example, it is possible to cite tetramethylammonium chloride, tetramethylammonium bromide, tetra-n-butylammonium chloride, tetra-n-butylammonium bromide, benzyltriethylammonium chloride, methyltrioctylammonium chloride, tetra-n-butylphosphonium chloride, tetra-n-butylphosphonium bromide and methyltriphenylphosphonium chloride.

Incidentally, a gas obtained after the reaction is passed through a cooled condenser and then collected in a collection vessel to be liquefied, thereby obtaining cis-1,3,3,3-tetrafluoropropene.

The distillation column used in the distillation operation is not limited in terms of material, and therefore columns formed of glass or stainless steel and those subjected to lining with tetrafluoroethylene resin, chlorotrifluoroethylene resin, vinylidene fluoride resin, PFA resin or glass at its interior are usable. The distillation column may be filled with a filler. Distillation is preferably conducted under normal or applied pressure condition, similar to the second step. The number of stages of the distillation column, required for conducting distillation is not particularly limited, but preferably 5 to 100 and more preferably 10 to 50.

By going through the above steps, trans- or cis-1,3,3,3-tetrafluoropropene can be produced with high purity.

EXAMPLES

Hereinafter, the present invention will be more specifically discussed with reference to Examples; however, the present invention is not limited to these Examples. By the way, "%" used for a composition analysis value represents "an areal %" of a composition obtained by measuring the reaction mixture directly by gas chromatography (a detector is FID unless otherwise specified).

Preparation Example 1

To 450 g of ion-exchanged water, 50 g of zirconyl chloride was dissolved. Thereafter, 500 g of γ-alumina (KHS46 available from SUMICA ALCHEM Co., Ltd.) that had previously been subjected to fluorination in the gas phase was immersed in the thus prepared solution. Two days later, these were poured into a Buchner funnel to separate liquid, then exposed to air until the surface was dried, and then put into a rotary evaporator to perform drying under reduced pressure. Into a jacketed reaction tube (27.2 mm inner diameter, 700 mm length) formed of YUS270 (stainless steel) made capable of communicating a heating medium, 350 ml of the thus prepared catalyst was charged. The heating medium was increased in temperature with flowing nitrogen at 200 ml/min, followed by drying at 300° C. until no more water went out. Thereafter, hydrogen fluoride was introduced into the reaction tube at 1 to 2 g/min so that the temperature of the catalyst did not exceed 350° C., while increasing the amount of nitrogen if heat was generated. After the heat generation had disappeared, the temperature was increased to 350° C. The preparation of catalyst was ended when it was confirmed that heat was no longer generated.

Preparation Example 2

Into a jacketed reaction tube (27.2 mm inner diameter, 700 mm length) formed of YUS270 (stainless steel) made capable of communicating a heating medium, 350 ml of γ-alumina (KHS46 available from SUMICA ALCHEM Co., Ltd.) that had previously been subjected to fluorination in the gas phase was charged. The heating medium was increased in temperature with flowing nitrogen at 200 ml/min, followed by drying at 300° C. until no more water went out. Thereafter, hydrogen fluoride was introduced into the reaction tube at 1 to 2 g/min so that the temperature of the catalyst did not exceed 350° C., while increasing the amount of nitrogen if heat was generated. After the heat generation had disappeared, the temperature was increased to 350° C. The preparation of catalyst was ended when it was confirmed that heat was no longer generated.

Preparation Example 3

By adding 300 g of water to 300 g of 40% chromium chloride aqueous solution (available from NIHON KAGAKU SANGYO CO., LTD.), 20% chromium chloride aqueous solution was prepared. A 1 liter beaker was charged with 500 ml of activated carbon (available from Japan EnviroChemicals, Ltd. under the trade name of Shirasagi G2X). The 20% chromium chloride aqueous solution that had previously been prepared was poured into the beaker and slowly stirred until bubbles were no longer generated, followed by standing it still for 24 hours. The content was poured into a Buchner funnel to separate liquid, then exposed to air until the surface was dried, and then put into a rotary evaporator to perform drying under reduced pressure. Into a jacketed reaction tube (27.2 mm inner diameter, 700 mm length) formed of YUS270 (stainless steel) made capable of communicating a heating medium, 350 ml of the thus prepared catalyst was charged. The heating medium was increased in temperature with flowing nitrogen at 200 ml/min, followed by drying at 300° C. until no more water went out. Thereafter, hydrogen fluoride was introduced into the reaction tube at 1 to 2 g/min so that the temperature of the catalyst did not exceed 350° C., while increasing the amount of nitrogen if heat was generated. After the heat generation had disappeared, the temperature was increased to 350° C. The preparation of catalyst was ended when it was confirmed that heat was no longer generated.

Preparation Example 4

By adding 300 g of water to 300 g of 40% chromium chloride aqueous solution (available from NIHON KAGAKU SANGYO CO., LTD.), 20% chromium chloride aqueous solution was prepared. Thereafter, 500 g of γ-alumina (KHS46 available from SUMICA ALCHEM Co., Ltd.) that had previously been subjected to fluorination in the gas phase was immersed in the previously prepared solution. Two days later, these were poured into a Buchner funnel to separate liquid, then exposed to air until the surface was dried, and then put into a rotary evaporator to perform drying under reduced pressure. Into a jacketed reaction tube (27.2 mm inner diameter, 700 mm length) formed of YUS270 (stainless steel) made capable of communicating a heating medium, 350 ml of the thus prepared catalyst was charged. The heating medium was increased in temperature with flowing nitrogen at 200 ml/min, followed by drying at 300° C. until no more water went out. Thereafter, hydrogen fluoride was introduced into the reaction tube at 1 to 2 g/min so that the temperature of the catalyst did not exceed 350° C., while increasing the amount of nitrogen if heat was generated. After the heat generation had disappeared, the temperature was increased to 350° C. The preparation of catalyst was ended when it was confirmed that heat was no longer generated.

Preparation Example 5

By adding 150 g of water to 150 g of 40% chromium chloride aqueous solution (available from NIHON KAGAKU SANGYO CO., LTD.), 20% chromium chloride aqueous solution was prepared. Meanwhile, 60 g of copper chloride (anhydride) available from Wako Pure Chemical Industries, Ltd. was dissolved in 240 g of water. These two solutions were mixed thereby obtaining a chromium-copper aqueous solution. Thereafter, 500 g of γ-alumina (KHS46 available from SUMICA ALCHEM Co., Ltd.) that had previously been subjected to fluorination in the gas phase was immersed in the previously prepared solution. Two days later, these were poured into a Buchner funnel to separate liquid, then exposed to air until the surface was dried, and then put into a rotary evaporator to perform drying under reduced pressure. Into a jacketed reaction tube (27.2 mm inner diameter, 700 mm length) formed of YUS270 (stainless steel) made capable of communicating a heating medium, 350 ml of the thus prepared catalyst was charged. The heating medium was increased in temperature with flowing nitrogen at 200 ml/min, followed by drying at 300° C. until no more water went out. Thereafter, hydrogen fluoride was introduced into the reaction tube at 1 to 2 g/min so that the temperature of the catalyst did not exceed 350° C., while increasing the amount of nitrogen if heat was generated. After the heat generation had disappeared, the temperature was increased to 350° C. The preparation of catalyst was ended when it was confirmed that heat was no longer generated.

Comparative Example 1

The reaction tube filled with the catalyst, which was prepared according to Preparation Example 1, was heated to 200° C. As soon as the temperature was stabilized, HFC-245fa was fed into the reaction tube at 6.6 g/min and the supply of nitrogen was suspended. It was confirmed by calculation that the contact time was 8.4 seconds. Two hours later, sampling was carried out after the temperature distribution was confirmed to have been stabilized. Then, the reaction tube was rinsed with water to remove the acid content, followed by conducting an analysis by means of gas chromatography.

Comparative Example 2

The reaction was conducted by repeating the procedure of Comparative Example 1, with the exception that the reaction tube filled with the catalyst prepared according to Preparation Example 1 was heated to 345° C. and HFC-245fa was supplied thereto at 6.1 g/min. It was confirmed by calculation that the contact time was 9.1 seconds.

Comparative Example 3

The reaction was conducted by repeating the procedure of Comparative Example 1, with the exception that the reaction tube filled with the catalyst prepared according to Preparation Example 1 was heated to 200° C. and the pressure inside the reaction tube was adjusted by a vacuum pump to 1 kPa and HFC-245fa was supplied thereto at 6.1 g/min. It was confirmed that the contact time in terms of real condition was about 0.1 second.

Example 1

The reaction was conducted by repeating the procedure of Comparative Example 1, with the exception that the reaction tube filled with the catalyst prepared according to Preparation Example 1 was heated to 345° C. and the pressure inside the reaction tube was adjusted by a vacuum pump to 1 kPa and HFC-245fa was supplied thereto at 6.9 g/min. It was confirmed that the contact time in terms of real condition was about 0.1 second.

Example 2

The reaction was conducted by repeating the procedure of Comparative Example 1, with the exception that the reaction tube filled with the catalyst prepared according to Preparation Example 1 was heated to 345° C. and the pressure inside the reaction tube was adjusted by a vacuum pump to 0.6 kPa and HFC-245fa was supplied thereto at 2.4 g/min. It was confirmed that the contact time in terms of real condition was about 0.1 second.

Comparative Example 4

The reaction tube filled with the catalyst, which was prepared according to Preparation Example 2, was heated to 300° C. As soon as the temperature was stabilized, HFC-245fa was fed into the reaction tube at 6.1 g/min and the supply of nitrogen was suspended. It was confirmed by calculation that the contact time was 9.1 seconds. Two hours later, sampling was carried out after the temperature distribution was confirmed to have been stabilized. Then, the reaction tube was rinsed with water to remove the acid content, followed by conducting an analysis by means of gas chromathography.

Example 3

The reaction was conducted by repeating the procedure of Comparative Example 4, with the exception that the pressure inside the reaction tube filled with the catalyst prepared according to Preparation Example 2 was adjusted by a vacuum pump to 0.6 kPa and HFC-245fa was supplied thereto at 6.1 g/min. It was confirmed that the contact time in terms of real condition was about 0.1 second.

Comparative Example 5

The reaction tube filled with the catalyst, which was prepared according to Preparation Example 3, was heated to 300° C. As soon as the temperature was stabilized, HFC-245fa was fed into the reaction tube at 6.1 g/min and the supply of nitrogen was suspended. It was confirmed by calculation that the contact time was 9.1 seconds. Two hours later, sampling was carried out after the temperature distribution was confirmed to have been stabilized. Then, the reaction tube was rinsed with water to remove the acid content, followed by conducting an analysis by means of gas chromatography.

Example 4

The reaction was conducted by repeating the procedure of Comparative Example 5, with the exception that the pressure inside the reaction tube filled with the catalyst prepared according to Preparation Example 3 was adjusted by a vacuum pump to 0.6 kPa and HFC-245fa was supplied thereto at 6.1 g/min. It was confirmed that the contact time in terms of real condition was about 0.1 second.

Comparative Example 6

The reaction tube filled with the catalyst, which was prepared according to Preparation Example 4, was heated to 300° C. As soon as the temperature was stabilized, HFC-245fa was fed into the reaction tube at 6.1 g/min and the supply of nitrogen was suspended. It was confirmed by calculation that the contact time was 9.1 seconds. Two hours later, sampling was carried out after the temperature distribution was confirmed to have been stabilized. Then, the reaction tube was rinsed with water to remove the acid content, followed by conducting an analysis by means of gas chromatography.

Example 5

The reaction was conducted by repeating the procedure of Comparative Example 5, with the exception that the pressure inside the reaction tube filled with the catalyst prepared according to Preparation Example 4 was adjusted by a vacuum pump to 0.6 kPa and HFC-245fa was supplied thereto at 6.1 g/min. It was confirmed that the contact time in terms of real condition was about 0.1 second.

Comparative Example 7

The reaction tube filled with the catalyst, which was prepared according to Preparation Example 5, was heated to 280° C. As soon as the temperature was stabilized, HFC-245fa was fed into the reaction tube at 6.1 g/min and the supply of nitrogen was suspended. It was confirmed by calculation that the contact time was 9.1 seconds. Two hours later, sampling was carried out after the temperature distribution was confirmed to have been stabilized. Then, the reaction tube was rinsed with water to remove the acid content, followed by conducting an analysis by means of gas chromatography.

Example 6

The reaction was conducted by repeating the procedure of Comparative Example 5, with the exception that the pressure inside the reaction tube filled with the catalyst prepared according to Preparation Example 5 was adjusted by a vacuum pump to 0.6 kPa and HFC-245fa was supplied thereto at 6.1 g/min. It was confirmed that the contact time in terms of real condition was about 0.1 second.

Results of the above will be shown in Table 1.

TABLE 1

|  | HFC-245fa (g/min) | Contact Time (sec.) | Pressure (kPa) | Temperature (° C.) | 1234E (G C %) | HFC-245fa (G C %) | 1234Z (G C %) | Conversion Ratio (%) |
|---|---|---|---|---|---|---|---|---|
| Comparative Example 1 | 6.6 | 8.4 | 101 | 200 | 11.36 | 86.7 | 1.89 | 13.3 |
| Comparative Example 2 | 6.1 | 9.1 | 101 | 345 | 67.92 | 14.66 | 17.18 | 85.34 |
| Comparative Example 3 | 6.1 | 0.1 | 1 | 200 | 23.72 | 72.3 | 3.9 | 27.7 |

TABLE 1-continued

|  | HFC-245fa (g/min) | Contact Time (sec.) | Pressure (kPa) | Temperature (° C.) | 1234E (G C %) | HFC-245fa (G C %) | 1234Z (G C %) | Conversion Ratio (%) |
|---|---|---|---|---|---|---|---|---|
| Example 1 | 6.9 | 0.1 | 1 | 345 | 77.04 | 3.07 | 19.65 | 96.93 |
| Example 2 | 2.4 | 0.1 | 0.6 | 345 | 78.69 | 0.73 | 20.03 | 99.27 |
| Comparative Example 4 | 6.1 | 9.1 | 101 | 300 | 63.65 | 22.85 | 13.46 | 77.15 |
| Example 3 | 6.1 | 0.1 | 0.6 | 300 | 73.06 | 9.92 | 16.97 | 90.08 |
| Comparative Example 5 | 6.1 | 9.1 | 101 | 300 | 62.22 | 24.28 | 13.37 | 75.72 |
| Example 4 | 6.1 | 0.1 | 0.6 | 300 | 79.88 | 2.36 | 17.71 | 97.64 |
| Comparative Example 6 | 6.1 | 9.1 | 101 | 300 | 61.23 | 25.27 | 13.12 | 74.73 |
| Example 5 | 6.1 | 0.1 | 0.6 | 300 | 80.01 | 1.23 | 18.28 | 98.77 |
| Comparative Example 7 | 6.1 | 9.1 | 101 | 280 | 34.66 | 58.78 | 6.08 | 41.22 |
| Example 6 | 6.1 | 0.1 | 0.6 | 300 | 64.71 | 21.46 | 13.78 | 78.54 |

Example 7

After the analysis in Example 6 by means of gas chromatography, a produced gas ejected from the reactor was blown into water to remove an acid gas. The gas product was then passed through a drying tower charged with molecular sieve 3A (a trade name), and collected by a dry ice-acetone trap. The reaction was continued for 24 hours, upon which 3871 g of a reaction product was collected. As a result of analyzing the thus collected organic substance by means of gas chromatography, the substance was confirmed to be composed of 64.3% of trans-1234ze, 13.9% of cis-1234ze and 21.5% of HFC-245fa.

Thereafter the reaction product was subjected to distillation. As the first fraction, trans-1234ze was distilled (the purity of the distilled trans-1234 ze was 99.9%), thereby obtaining 579 g of a fraction where cis-1234 ze was condensed. As a result of analyzing the fraction containing cis-1234ze, it was confirmed that this fraction was composed of 18.42% of HFC-245fa and 81.5% of cis-1234ze.

Subsequently, a 1 L autoclave formed of SUS316 was equipped with a double pipe condenser formed of SUS316, and then an ethylene glycol aqueous solution of −5° C. was circulated through a jacket of the condenser. The autoclave was charged with 4.0 g of tetra-n-butylammonium bromide, 38.68 g of 48 wt % potassium hydroxide aqueous solution (i.e. 0.33 mol of potassium hydroxide). The autoclave was subjected to pressure reduction by means of a vacuum pump. The autoclave was then cooled with ice water, followed by introducing 500 g (4.25 mol) of the organic substance that contained cis-1234ze (18.42% of HFC-245fa and 81.5% of cis-1234ze) thereinto. The organic substance was stirred by a stirrer, and then the autoclave was immersed in a 40-45° C. hot bath to be increased in temperature. Heating was continued for 19 hours. After the termination of the reaction, the cooling of the condenser was suspended, and 465 g of the reaction product was collected in a glass trap cooled with dry ice-acetone. It was confirmed that the conversion ratio of HFC-245 fa was 99.99% and the reaction product was composed of 13.1% of trans-1234 ze and 86.3% of cis-1234ze. The reaction product was purified by distillation thereby obtaining 386 g of cis-1234 ze at a purity of 99.9%

Even if HFC-245fa is thus contained in cis-1,3,3,3-tetrafluoropropene, HFC-245fa can be removed by being reacted with a base and then subjected to a distillation operation, with which it becomes possible to obtain cis- or trans-1,3,3,3-tetrafluoropropene with high purity.

INDUSTRIAL APPLICABILITY

The target compound of the present invention, i.e. 1,3,3,3-tetrafluoropropene, is adaptable for use as an intermediate of medicines, agrichemicals or functional materials, a refrigerant, a working fluid, a fireproof protective gas for molten magnesium/magnesium alloy production.

The invention claimed is:

1. A method for producing 1,3,3,3-tetrafluoropropene comprising the steps of:
    causing a dehydrofluorination reaction of 1,1,1,3,3-pentafluoropropane in the gas phase and in the presence of a catalyst thereby producing 1,3,3,3-tetrafluoropropene, wherein the dehydrofluorination reaction is carried out at a pressure inside the reaction system of from 0.001 to 90 kPa (absolute pressure) at a reaction temperature ranging from 250 to 600° C.;
    separating and removing hydrogen fluoride from a reaction mixture produced by the dehydrofluorination reaction of 1,1,1,3,3-pentafluoropropane, wherein the reaction mixture contains 1,3,3,3-tetrafluoropropene, unreacted 1,1,1,3,3-pentafluoropropane, organic impurities and hydrogen fluoride;
    subjecting the mixture obtained after removing hydrogen fluoride to distillation, wherein a fraction obtained by distillation comprises: trans-1,3,3,3-tetrafluoropropene; and cis-1,3,3,3-tetrafluoropropene containing 1,1,1,3,3-pentafluoropropane; and
    reacting the cis-1,3,3,3-tetrafluoropropene containing 1,1,1,3,3-pentafluoropropane with a base and then performing distillation, to obtain cis-1,3,3,3-tetrafluoropropene which does not substantially contain 1,1,1,3,3-pentafluoropropane.

2. The method as claimed in claim 1, wherein the cis-1,3,3,3-tetrafluoropropene which does not substantially contain 1,1,1,3,3-pentafluoropropane has a mole ratio represented by 1,1,1,3,3-pentafluoropropane/cis-1,3,3,3-tetrafluoropropene ranging from 1/100 to 1/1000.

3. The method as claimed in claim 1, wherein the base is a hydroxide of an alkali metal, or a hydroxide of an alkaline earth metal.

4. The method as claimed in claim 3, wherein the hydroxide of an alkali metal is lithium hydroxide, sodium hydroxide or potassium hydroxide.

5. The method as claimed in claim 3, wherein the hydroxide of an alkaline earth metal is calcium hydroxide, magnesium hydroxide or strontium hydroxide.

* * * * *